US010400240B1

(12) United States Patent
Marti-Arbona et al.

(10) Patent No.: US 10,400,240 B1
(45) Date of Patent: Sep. 3, 2019

(54) COMPOSITIONS AND METHODS FOR RNA-BASED ANTIMICROBIAL DRUG TARGETING

(71) Applicant: Los Alamos National Security, LLC, Los Alamos, NM (US)

(72) Inventors: Ricardo Marti-Arbona, Los Alamos, NM (US); Scott Hennelly, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 0 days.

(21) Appl. No.: 15/884,265

(22) Filed: Jan. 30, 2018

Related U.S. Application Data

(60) Provisional application No. 62/452,217, filed on Jan. 30, 2017.

(51) Int. Cl.
*C07H 21/04* (2006.01)
*C12N 15/113* (2010.01)
*C12Q 1/18* (2006.01)

(52) U.S. Cl.
CPC .............. *C12N 15/113* (2013.01); *C12Q 1/18* (2013.01); *C12N 2310/14* (2013.01); *C12N 2310/531* (2013.01); *C12N 2320/10* (2013.01)

(58) Field of Classification Search
CPC .................................................... C12N 15/111
See application file for complete search history.

(56) References Cited

U.S. PATENT DOCUMENTS

2005/0227940 A1* 10/2005 Rossi .................... C12N 15/111 514/44 A

OTHER PUBLICATIONS

Cardona, Silvia T. et al., "An expression vector containing a rhamnose-inducible promoter provides rightly regulated gene expression in Burkholderia cenocepacia", Plasmid, vol. 54, pp. 219-228 (2005).

Chong, Chan-Eng et al., "In silico analysis of Burkholderia pseudomallei genome sequence for potential drug targets", School of Biosciences and Biotechnology, Malaysia, Malaysia Genome Institute (2006.

Hamad, Mohamad A. et al., "An allelic exchange system for compliant genetic manipulation of the select agents Burkholderia pseudomallei and Burkholderia mallei", Gene, vol. 430, pp. 123-131 (2009).

Wilson, Kevin S. et al., "Transcription termination at intrinsic terminators: The role of the RNA hairpin", Proc. Natl. Acad. Sci. USA, vol. 92, pp. 8793-8797 (1995).

* cited by examiner

*Primary Examiner* — Kimberley Chong
(74) *Attorney, Agent, or Firm* — Lewis Roca Rothgerber Christie LLP

(57) ABSTRACT

A ribonucleic acid (RNA) based modular regulatory element (MRE) for inhibiting translation of a target gene transcript in an organism (e.g. a pathogen) includes a first segment of RNA capable of forming a stem loop structure, a second segment of RNA downstream of the first segment of RNA and having a target sequence capable of binding to the target gene transcript (or polycistron lead gene transcript), and a third segment of RNA downstream of the second segment of RNA and being capable of forming a terminator hairpin downstream of the target sequence. Methods for assaying the role of a putative target gene in an organism include inhibiting expression of various target genes using the RNA-based MRE.

3 Claims, 13 Drawing Sheets
(13 of 13 Drawing Sheet(s) Filed in Color)
Specification includes a Sequence Listing.

Modular Regulatory Element (MRE)/ Riboregulator RNA (5)

COMPOSITIONS AND METHODS FOR RNA-BASED ANTIMICROBIAL DRUG TARGETING

CROSS-REFERENCE TO RELATED APPLICATION(S)

The present application claims priority to and the benefit of U.S. Provisional Application Ser. No. 62/452,217 filed on Jan. 30, 2017, entitled "COMPOSITIONS AND METHODS FOR RNA-BASED ANTIMICROBIAL DRUG TARGETING," the entire content of which is incorporated herein by reference.

STATEMENT REGARDING FEDERALLY SPONSORED RESEARCH OR DEVELOPMENT

The United States government has certain rights in this invention pursuant to Contract No. DE-AC52-06NA25396 between the United States Department of Energy and Los Alamos National Security, LLC for the operation of Los Alamos National Laboratory.

INCORPORATION BY REFERENCE

The present application contains a Sequence Listing which has been submitted in ASCII format via EFS-Web and is hereby incorporated by reference in its entirety. Said ASCII copy, created on Jan. 29, 2018, is named 147368SEQLISTING.txt and is 5,083 bytes in size.

BACKGROUND

The majority of currently used antibiotics are compromised by the emergence of multiple drug resistance (MDR) mechanisms. Antimicrobial resistance is an unavoidable effect of continuous use of antibiotics rendering humans and animals vulnerable to MDR. It has been postulated that some parts of the world are in, or could soon be in, a post-antibiotic era. At this time, there are fewer than 40 protein targets for antimicrobial treatments, and unfortunately, there is a lack of effective methods to identify and characterize novel or unique therapeutic targets.

SUMMARY

In some embodiments of the present invention, a modular regulatory element (MRE) composition is composed of a ribonucleic acid (RNA) that inhibits translation of a target gene transcript. The MRE composition as presented in the present disclosure may also be referred to as an "RNA Regulator," a "Riboregulator", or "Riboregulator RNA." This RNA includes a first segment of RNA capable of forming a stem loop structure, a second segment of RNA downstream of the first segment of RNA and including a targeting sequence capable of binding to the target gene transcript, and a third segment of RNA downstream of the second segment of RNA and being capable of forming a terminator hairpin downstream of the targeting sequence. In some embodiments, the targeting sequence is capable of binding to a ribosomal binding site (RBS) of the target gene transcript. In some embodiments, the targeting sequence is complementary to the RBS of the target gene transcript.

In some embodiments of the present invention, a method of assaying the essentialness of a putative target gene in an organism (e.g., a pathogen) includes culturing the organism expressing the modular regulatory element (MRE), and binding the MRE to the ribosomal binding site (RBS) of a transcript of the putative essential gene to inhibit translation of the putative essential gene. As used herein, an "essential gene" refers to a gene that is required for growth of the organism and includes absolute essential genes and conditional essential genes. In some instances, the essential gene is an absolute essential gene as the gene is required for growth of the organism in any condition. In other instances, the essential gene is a conditional essential gene and is required for growth of the organism in the presence of an additional factor such as an antibiotic. In some embodiments, binding the MRE to the RBS of a transcript of the putative essential gene includes expressing the modular regulatory element (MRE) composition for inhibiting translation of a target gene transcript as described herein. In some embodiments, the putative essential gene in the organism is not found in humans (e.g., no homologs of the pathogen gene are found in humans). In some embodiments, the method of assaying a putative essential gene in an organism also includes adding an antibiotic to a culture of the organism either prior to or after the binding of the MRE to the RBS of the transcript. In some embodiments of the present invention, the activity of the MRE is determined by monitoring the growth of the organism or by high throughput sequencing.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Multiple drug resistant (MDR) pathogens may be defeated by at least one of two main paths: 1) identification of novel antimicrobial drugs and therapies; and/or 2) deactivation of the current MDR mechanisms, thereby making the pathogen susceptible to existing antibiotic therapies. Some embodiments of the present invention are directed to the inhibition of genes that are essential for the MDR pathogen or the MDR mechanism in the pathogen.

For example, embodiments of the present invention include methods for identifying putative target genes in a selected organism (e.g., a pathogen) testing the putative target gene by deactivating the expression of the gene. More specifically, embodiments of the present invention include methods for deactivating a putative essential target gene by binding the ribosomal binding site (RBS) of the putative essential target gene transcript, and thereby blocking translation.

Also, as used herein, the term "transcript" refers to the messenger ribonucleic acid (mRNA) formed from transcription of the gene. As used herein, "deactivation," "deactivating," and like terms in reference to a gene refer to inhibition of the mRNA translation of the gene's mRNA to protein. Deactivation of a gene by inhibition of a gene's mRNA translation is also referred to as "inhibition of expression," "inhibition of gene expression," "inhibition of translation" and "MRE activity". As used herein, "heterologous expression" refers to the expression nucleic acid vectors (e.g., DNA plasmid vectors) that are introduced and are exogenous to the host organism.

As used herein, "putative target gene," putative essential gene," "putative essential target gene," and "target gene," are used interchangeably to refer to the particular candidate gene that is the binding target of the MRE to be assayed for its role in the growth of the organism either under normal growth conditions or in the presence of an antibiotic.

In some embodiments, methods of screening for multidrug resistance (MDR) mechanisms include testing a putative target gene by inhibiting expression of the target gene in the presence of an antibiotic to determine the effect of the inhibited gene on MDR resistance and/or bacterial physiology in the presence of the antibiotic.

Figure 1:
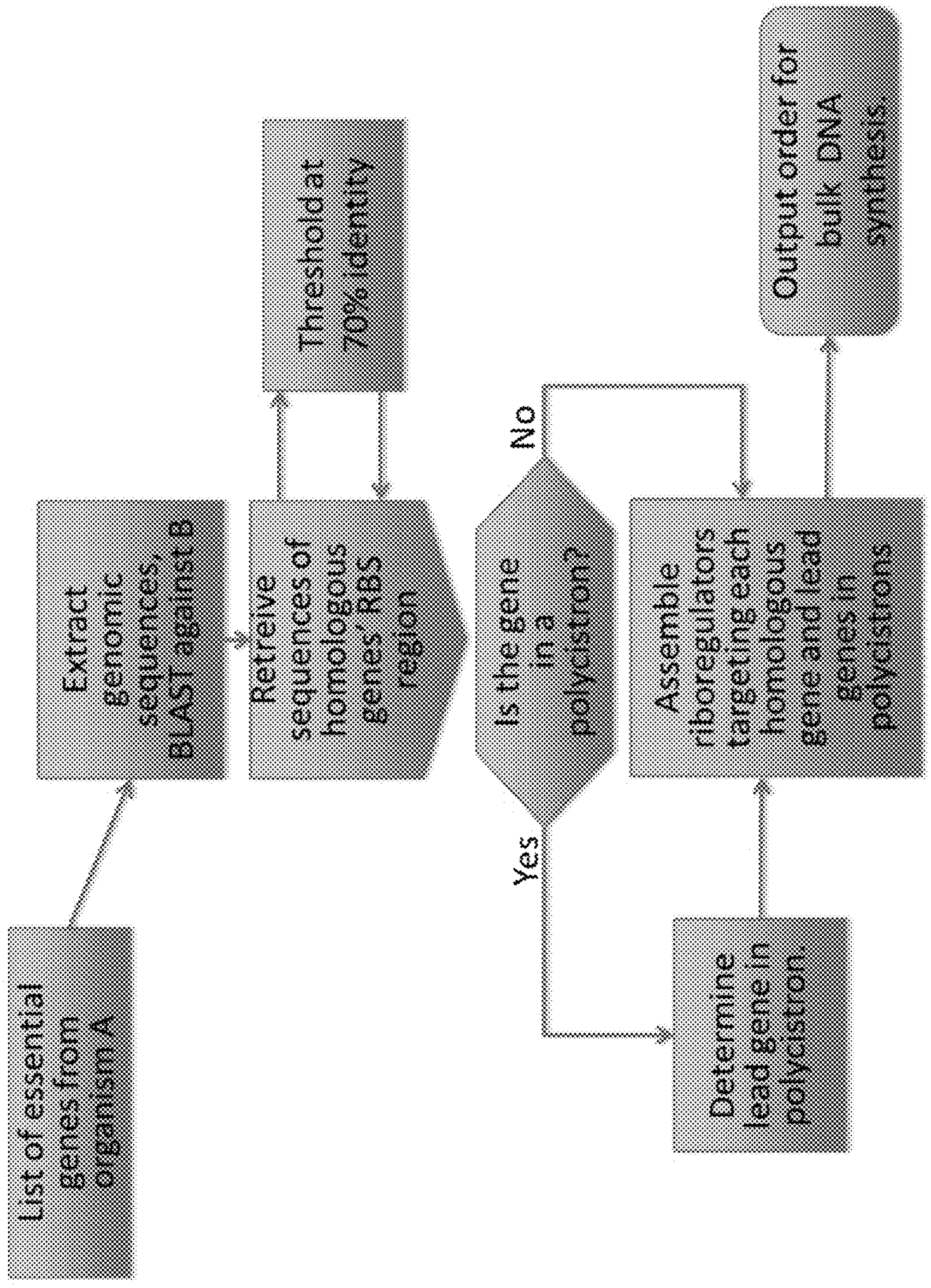
FIG. 1 is a flow chart diagram depicting the modular regulatory element (MRE) design and production, including the identification of a target sequence for a selected organism (organism A) using comparative alignment with organism B, according to embodiments of the present invention.

With reference to FIG. 1, in some embodiments of the present invention, a methodology for identifying and validating putative target genes in a target pathogen (organism B) includes determining a target sequence of the organism (Organism B) in silico by aligning all of the essential genes or genes known to be essential for multidrug resistance of a known selected organism designated as Organism A. Organism A is a characterized organism for which essential gene research has been previously performed (or suggested) and a list of essential genes are identified in an essential gene database. Accordingly, in some embodiments, the known essential genes of Organism A are aligned with a determined sequence of Organism B (the target organism) to retrieve the RBS sequences from all of the essential genes that are homologous (i.e., those with at least 70% identity) between Organisms A and B. Accordingly, the RBS sequences of the targeted essential genes are known as the "target sequences" and are more distinctly referred to as the RBS of the gene transcript, whereas the "targeting sequence" is the hybridizing RNA sequence that binds to the target sequence (e.g., the RBS) on the targeted gene transcript. In some embodiments of the present invention, if the putative essential gene is in a polycistron, then the lead gene in the polycistron is identified along with the corresponding RBS sequence for the lead gene. In some embodiments, the targeting sequence includes an RNA sequence that hybridizes to the RBS sequence of the targeted gene or another gene within the polycistron. In some embodiments, the targeting sequence also includes a flanking sequence that contains specific restriction sites used for direct cloning of the targeting sequence into the MRE. Accordingly, the targeting sequences for binding the putative essential genes of a target pathogen (Organism B) are identified based on comparative alignment of the essential genes with organism A.

Figure 2A:
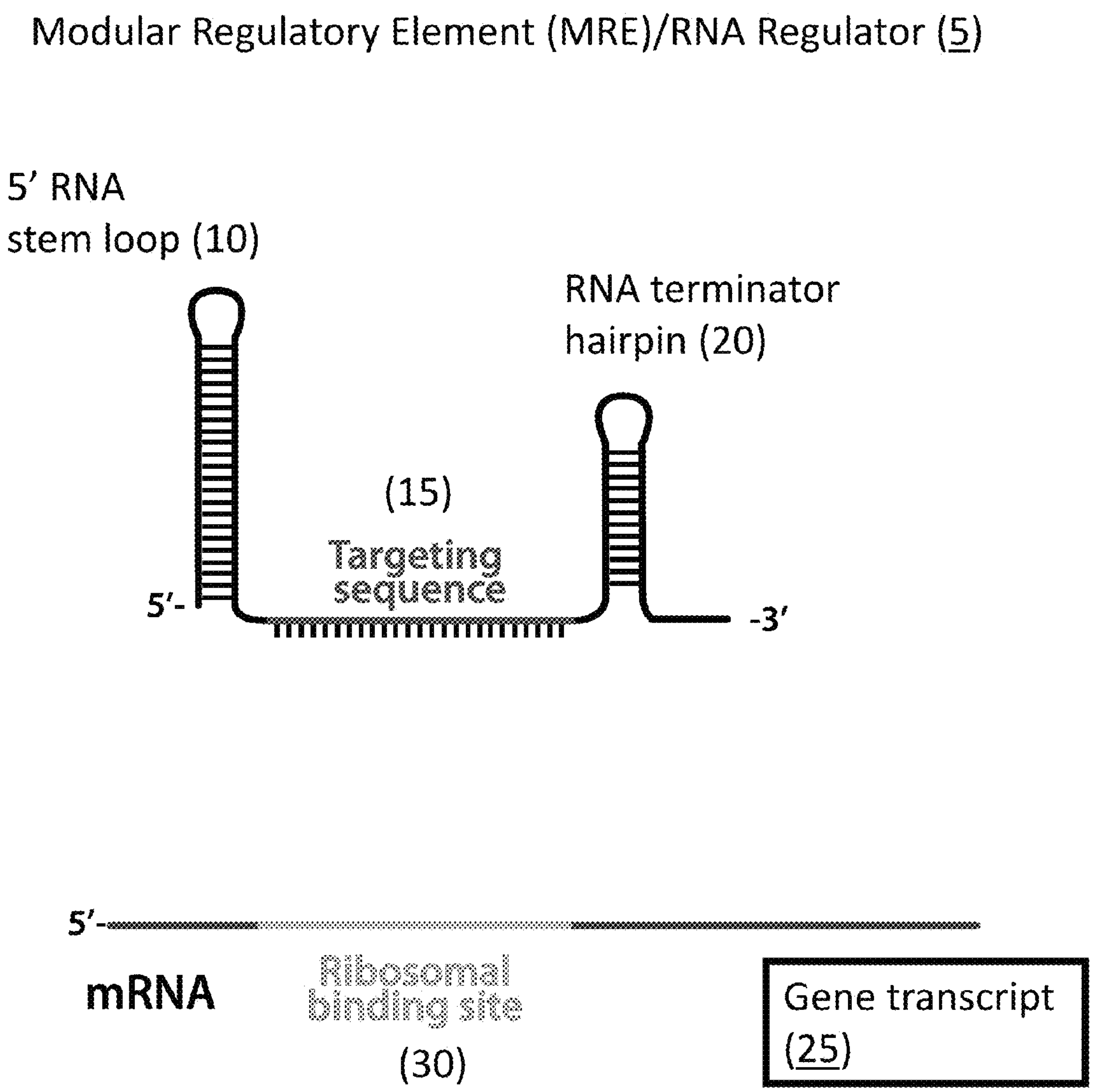
FIG. 2A is a schematic of an RNA-based modular regulatory element (MRE) (Riboregulator RNA (5)) having a 5' RNA stem loop (10), a variable target sequence (15) for binding to the ribosomal binding site (RBS) (30) on a putative target gene transcript (25) in an organism, and an RNA terminator hairpin sequence (20), according to embodiments of the present invention.
Figure 2B:
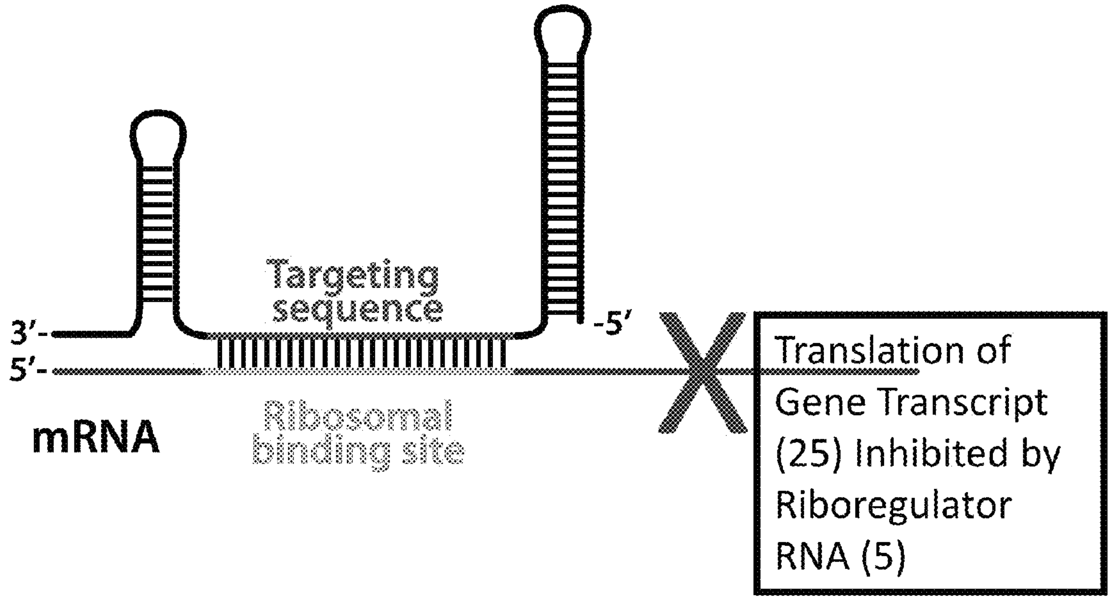
FIG. 2B is a schematic of the RNA Regulator (5) of FIG. 2A in its bound state to the RBS of the putative target gene transcript (25), thereby occluding translation of the putative target gene, according to embodiments of the present invention.
Figure 3:
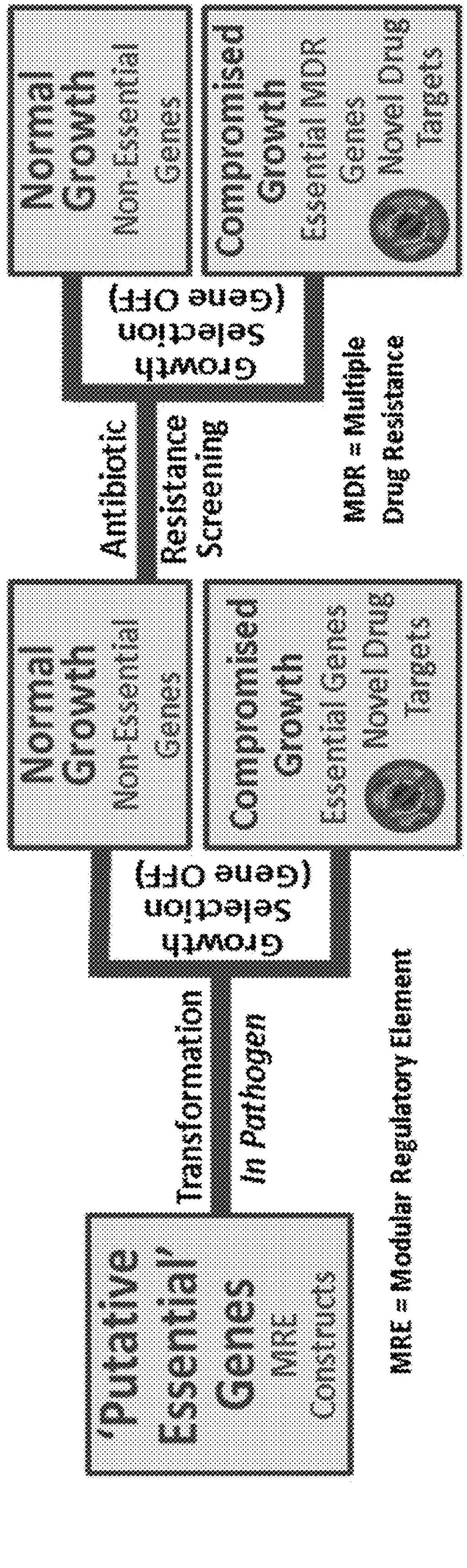
FIG. 3 is a flow diagram of the methods for targeting putative essential genes in organisms (e.g., *Burkholderia thailandensis* (*B. thailandensis* or Bt)) by assessing normal versus compromised growth of the organism when translation of a putative target gene is inhibited using an MRE (5) followed by addition of a selected antibiotic to Bt culture showing normal growth upon inhibition of a putative target gene in order to screen for antimicrobial resistance genes, according to embodiments of the present invention.

With reference to FIGS. 2A and 2B, according to embodiments of the present invention, a ribonucleic acid (RNA) composition for inhibiting translation of a putative (candidate) target gene is the RNA-based modular regulatory element (MRE) having a targeting sequence for binding to the ribosomal binding site (RBS) of a putative essential gene or a gene required for antimicrobial resistance (AMR) in an organism (e.g., a pathogen). This binding of the targeting sequence to the RBS of the target gene transcript inhibits expression of the target gene transcript.

According to embodiments of the present invention, a ribonucleic acid (RNA) composition for inhibiting translation of a target gene transcript, includes a first segment of RNA capable of forming a 5' stem loop structure (10), a second segment of RNA downstream of the first segment of RNA and having a targeting sequence (15) capable of binding to the target gene transcript (25), and a third segment of RNA downstream of the second segment of RNA that forms a 3' terminator (20) downstream of the targeting sequence.

With reference to FIG. 2A, an RNA Regulator (5) is an RNA composition that is a type of RNA-based MRE according to embodiments of the present disclosure. In some embodiments of the present invention, the RNA Regulator (which may also be referred to herein as a Riboregulator) is an RNA-based MRE made of a contiguous (e.g., consecutive) RNA sequence having a least three RNA segments. The first RNA segment is a 5' RNA stem loop (10), the second RNA segment is a targeting sequence (15), and the third RNA segment is a 3' terminator hairpin (20). While each segment of RNA may be characterized from another, the segments of RNA are part of one transcribed sequence unit. In some embodiments, the three segments of RNA may be separated by a flanking RNA sequence to provide spacing, and/or to allow for replacement of the segments of the RNA Regulator and/or to allow for insertion of the segments into an expression plasmid. The flanking RNA sequence may be referred to as a spacer RNA. In addition to flanking RNA sequences (or spacer RNA), the RNA segments may be separated by restriction site sequences thereby allowing for a segment to be enzymatically cut out of the contiguous sequence.

According to some embodiments of the present invention, an RNA Regulator (5) includes a strong 5' RNA stem-loop (e.g., $\Delta G° <= -40$ kcal/mol) and an efficient terminator (20) which together bracket the variable targeting sequence (15). As used herein, a 5' RNA stem loop includes any RNA sequence that forms a stem loop and has a free energy that is not more than about 54 kcal/mol. In some embodiments of the present invention, the 5' RNA stem loop (10) of the RNA Regulator (5) is SEQ ID NO: 1 AUUCGAGCCUCUCCUUCUAUCGGCGUGUGACGAGAAAUCGUAAUGCGUCGAUA GAAGGAGAGGUUCGAAU or SEQ ID NO: 2 UAAGCUUGGAGAGGAAGAUAGCUGCGUAAUGCUAAAGAGCAGUGUGCGGCUAU CUUCCUCUCCGAGCUUA.

In other embodiments, the RNA Regulator (5) includes a 5' RNA stem loop (10) having a smaller helix structure than the 5' RNA stem loop (10) of SEQ ID NO: 1 or SEQ ID NO: 2 so long as the smaller helix has a free energy that is not more than about 54 kcal/mol. For example, the 5' RNA stem loop (10) may form a helix structure that is a helix of 23 paired RNA basepairs ("helix-23") or a helix of 12 paired RNA basepairs ("helix-12"). In some embodiments, the 5' RNA stem loop (10) is a helix-23 of SEQ ID NO: 9 AUUCGAGCCAUCGGCGUGUGACGAGAAAUCGUAAUGCGUCGAUGGUUCGAAU or SEQ ID NO: 10 UAAGCUCGGUAGCCGCACACUGCUCUUUAGCAUUACGCAGCUACCAAGCUUA. In other embodiments, the 5' RNA stem loop (10) is a helix-12 of SEQ ID NO: 11 AUUCGAGCCAUAGAAAUAUGGUUCGAAU or SEQ ID NO: 12 UAAGCUCGGUAUCUUUAUACCAAGCUUA.

As used herein, the "targeting sequence" (15) of the RNA Regulator includes an RNA sequence that hybridizes to a region in the mRNA centered on the ribosome binding site (RBS) of the putative target gene. That is, the targeting sequence (15) for a putative essential gene in an organism includes the complementary RNA sequence that will hybridize to an mRNA sequence that spans from a position at least 20 nucleotide bases 5' (upstream) of the RBS translational start site to a position at least 20 bases 3' (downstream) to the RBS translational start site. The targeting sequences are complementary to and overlap the region spanning the ribosomal binding site (RBS) in a targeted essential gene's mRNA. The specific interaction of the RNA Regulator with the mRNA prevents translational initiation (e.g., ribosome binding), effectively abrogating expression.

As discussed herein, the RNA Regulator (5) also includes a 3' terminator hairpin (20), also referred to herein as a 3' terminator (20). As used herein, the 3' terminator or 3' terminator hairpin (20) includes any suitable RNA terminator hairpin for the target organism. In some embodiments, the 3' terminator (20) has an RNA sequence of SEQ ID NO: 3 AUCAAUAAAACGAAAGGCUCAGUCGAAAGACUGGGCCUUUCGUUUUAUCUGUUG With reference to FIG. 2B, binding of the targeting sequence (15) of the RNA Regulator to the cognate RBS (30) on the targeted mRNA gene transcript (25) occludes the RBS from being bound by the ribosome for initiation of translation thereby inhibiting gene expression.

Figure 4A:
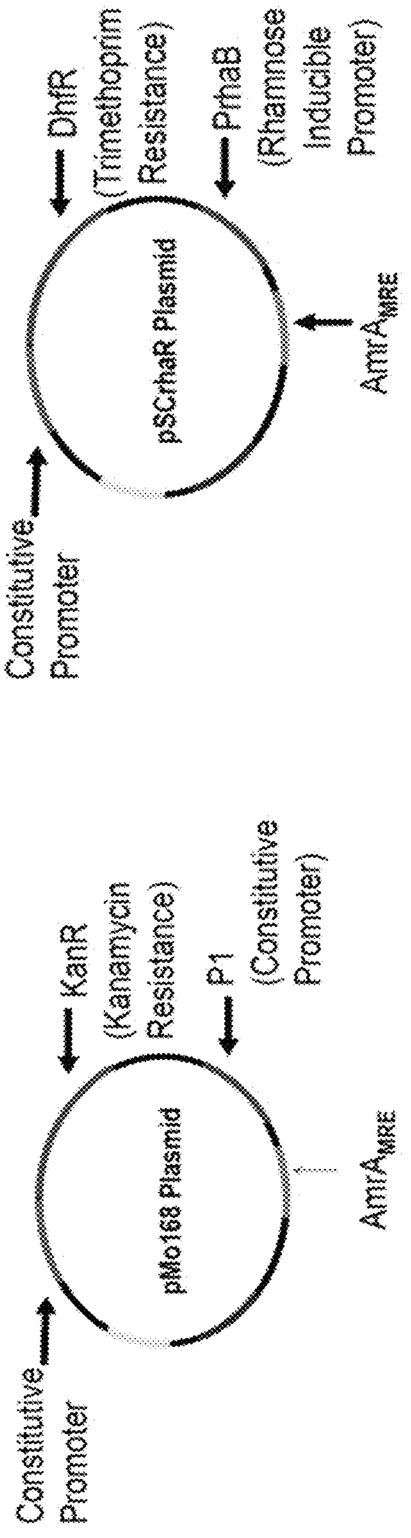
FIG. 4A is a schematic of the pMo168 plasmid vector having a mobilization element for transfer into a target organism by tri-parental mating having the specific MRE sequence for targeting the AmrA gene ($Amr_{AMRE}$) driven by the strong P1 promoter for constitutive expression in *B. thailandensis* (Bt), and a schematic of the pSCPrhaB2 plasmid having a modular regulatory element (MRE) for targeting the AmrA gene ($Amr_{AMRE}$) under the control of the rhamnose inducible promoter (PrhaB), according to embodiments of the present invention.

The components of the RNA Regulator (e.g., the 5' stem loop, the target sequencing and the 3' terminator) are modular, allowing for easy exchange of the targeting sequences using unique restriction sites in the MRE and Gibson assembly techniques. In some embodiments of the present invention, the components of the RNA Regulator are designed as a cassette for insertion into the pMO168 vector containing a mobilization element for transfer into a target organism by tri-parental mating, thus creating pMO168-MRE as depicted in FIG. 4A. In some embodiments of the present invention, a DNA vector encodes for an RNA Regulator having a 5' stem loop (5) of SEQ ID NO: 6 and a 3' terminator (20) of SEQ ID NO: 10.

In some embodiments, a DNA vector encodes for an RNA Regulator having a 5' stem loop (5) with helix-23 encoded by SEQ ID NO: 13 ATTCGAGCCATCGGCGTGTGACGAGAAATCGTAATGCGTCGATGGTTCGAAT or SEQ ID NO: 14 TAAGCTCGGTAGCCGCACACTGCTCTTTAGCATTACGCAGCTACCAAGCTTA, together with a 3' terminator (20) of SEQ ID NO: 7.

In some embodiments, a DNA vector encodes for an RNA Regulator having a 5' stem loop (5) with helix-12 encoded by SEQ ID NO: 15 ATTCGAGCCATAGAAATATGGTTCGAAT or SEQ ID NO: 16 TAAGCTCGGTATCTTTATACCAAGCTTA, together with a 3' terminator (20) of SEQ ID NO: 7.

In order to engineer an MRE to identify and validate putative essential genes that are critical to an organism's survival and multi drug resistance (MDR), the model pathogen *Burkholderia pseudomallei* was selected as organism A. The *B. pseudomallei* pathogen has 312 protein encoding genes that are not found in humans and have been computationally predicted to be essential for its survival and pathogenicity, as described in Chong et al., 2006, "In silico analysis of *Burkholderia pseudomallei* genome sequence for potential drug targets," *In Silico Biol* 6:341-346, the entire content of which is incorporated herein by reference. For validation of the 312 putative essential genes of *B. pseudomallei*, the non-pathogenic surrogate, *Burkholderia thailandensis* was used as the target organism, organism B.

Figure 4B:
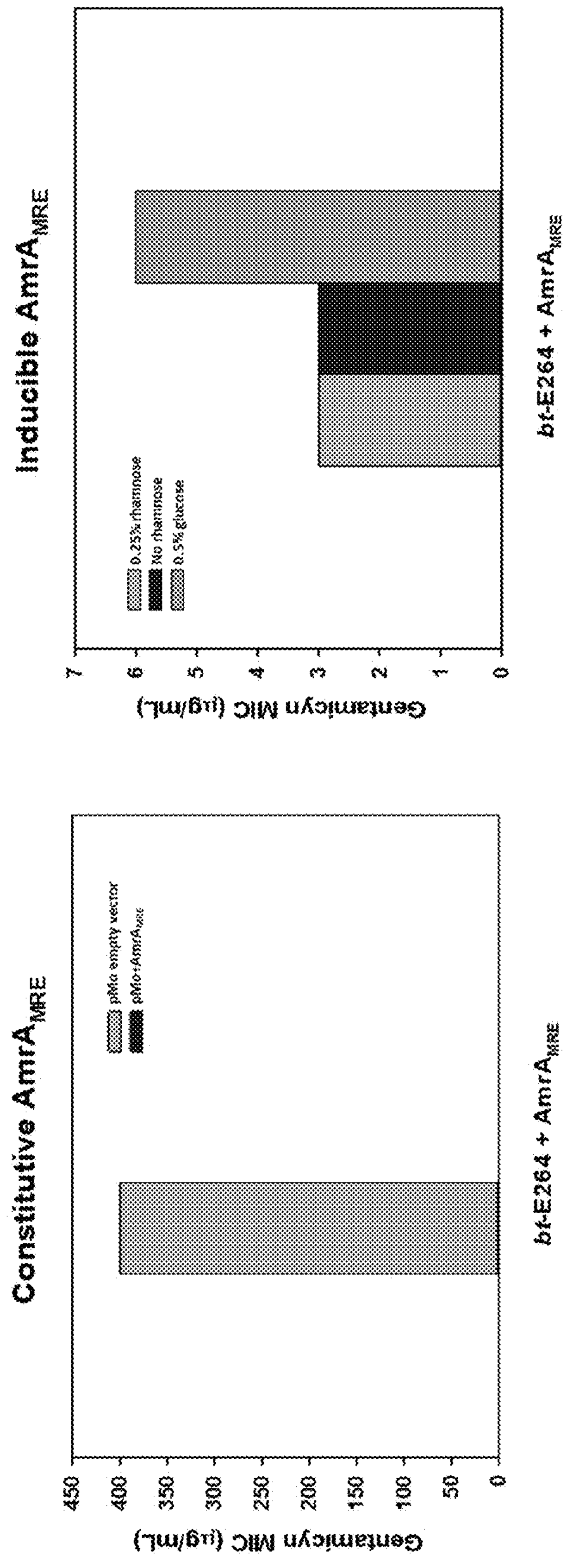
FIG. 4B shows a left graph depicting the growth of non-pathogenic Bt-E264 in the presence of gentamicin at the indicated minimum inhibitory concentration (MIC) μg/mL, without an RNA Regulator (pMO empty vector, green) and with the pMO168-$Amr_{AMRE}$ plasmid (pMo+$Amr_{AMRE}$, no growth (i.e., no maroon)) as shown in FIG. 4A constitutively expressing a target sequence that inhibits the AmrA gene translation, and a right graph depicting the growth of Bt-E264 transformed with the pSCPrhaB2 $Amr_{AMRE}$ plasmid as shown in FIG. 4A in the presence of gentamicin at the indicated minimum inhibitory concentration (MIC) μg/mL, in the presence of 0.25% rhamnose (green), no rhamnose (maroon), or 0.5% glucose (orange), according to embodiments of the present invention.

In order to assay the MRE for multi-drug resistance, an MDR assay was first validated in the *B. thailandensis* (Bt) target organism. The AmrAB multidrug efflux pump in Bt is known to confer resistance to the antibiotic gentamicin. By deactivating expression of the Bt-AmrA gene, the AmrAB efflux pump is not formed, rendering Bt susceptible to gentamicin. Accordingly, a vector (pMo168) as depicted in FIG. 4A was created allowing for the constitutive expression of an RNA Regulator targeting the RBS of the AmrA gene transcript ($Amr_{AMRE}$). This pMo168-$Amr_{AMRE}$ plasmid was transformed into Bt-E264 cells, and the resulting strain showed inhibited growth in the presence of gentamicin as shown in FIG. 4B. Accordingly, the $Amr_{AMRE}$ MRE is effective for inhibiting gene expression of the AmrA gene and increasing susceptibility of Bt-E264 cells to gentamicin.

The $Amr_{AMRE}$ was also expressed in a pSCPrhaB2 plasmid as depicted in FIG. 4A under a rhamnose-inducible promoter. This pSCPrhaB2-AmrAMRE plasmid was also transformed into Bt-E264 cells in the presence and absence of rhamnose. In the pSCPrhaB2-$Amr_{AMRE}$ plasmid, the PrhaB rhamnose inducible promoter controls the expression of the $Amr_{AMRE}$ MRE, and the results in FIG. 4A show that the PrhaB promoter is not able to fully control (e.g., shutdown) the expression of the $Amr_{AMRE}$ MRE in the absence of rhamnose and that the addition of 0.50% glucose helps the promoter to better control (e.g., shutdown) the expression of the $Amr_{AMRE}$ MRE in the absence of rhamnose. Additionally, as observed in FIG. 4B, the level of expression of the $Amr_{AMRE}$ MRE caused by the leakiness of the PrhaB promoter is sufficient to restore susceptibility of Bt-E264 to gentamicin.

Figure 5A:
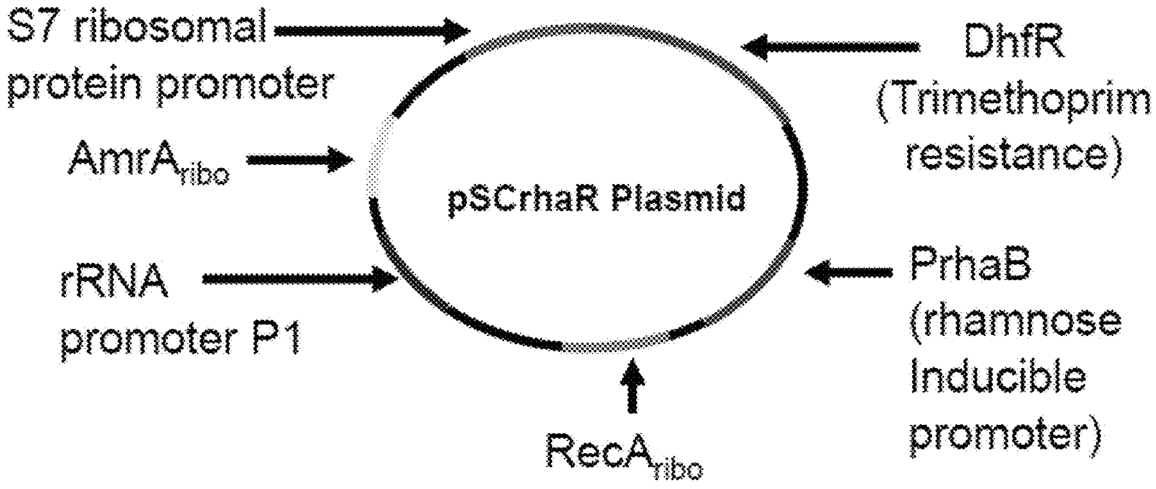
FIG. 5A is a schematic of the pSCPrhaB2 plasmid vector having a mobilization element and a rhamnose inducible promoter (PrhaB) for inducing expression of the specific MRE sequence ($iRec_{AMRE}$) for targeting the RecA gene in the presence of rhamnose and constitutive expression of the $cAmr_{AMRE}$ RNA Regulator for constitutive inhibition of the AmrA gene translation, according to embodiments of the present invention.

The RecA and AmrA genes were previously identified as co-resistance mechanisms against ciprofloxacin treatment. RecA is responsible for activating the repair of the DNA that is cleaved by the action of ciprofloxacin, and AmrA is part of the multidrug efflux pump, as described respectively in Thi et al., 2011, *J. Antimicrob Chemother*, "Effect of recA inactivation on mutagenesis of *Escherichia coli* exposed to sublethal concentrations of antimicrobials," 66: 531-538; and Podnecky et al., 2015, *Front Microbiol.*, "Efflux pump-mediated drug resistance in *Burkholderia,"* 6:305, the entire contents of both of which are incorporated herein by reference. For the MDR resistance assay, a vector as depicted in FIG. 5A was created allowing for the simultaneous constitutive expression of an MRE targeting the RBS of the AmrA gene transcript ($Amr_{AMRE}$) and an MRE targeting the RBS of RecA ($Rec_{AMRE}$) under a rhamnose inducible promoter.

For validation of the predicted putative essential genes, a library of 500 MREs was constructed having a targeting sequence for each of the identified putative essential genes. Some of the 312 putative essential genes (described in Chong et al., 2006, supra) were found within a polycistron, and in such cases an MRE was made with a targeting sequence (15) to the putative gene and a second MRE was made with a targeting sequence (15) to the lead gene of the polycistron. The addition of the MREs targeting the polycistron lead genes increased the MRE library from 312 to 500. The library of vectors containing the 500 MREs was constructed and transformed into Bt for culturing.

In some embodiments of the present invention, a method of assaying a putative essential gene in an organism includes culturing the organism and binding the ribosomal binding site (RBS) of a transcript of the putative essential gene to thereby inhibit translation of the putative essential gene. In some embodiments, a method of assaying a putative essential gene in an organism includes culturing the organism, and binding the ribosomal binding site (RBS) of a transcript of the lead gene of a polycistron gene cluster that includes the putative essential gene to thereby inhibit translation of the putative essential gene. In some embodiments, the binding of the RBS of a transcript of the putative essential gene includes transforming the organism with a vector expressing an RNA composition (RNA Regulator)(5) targeting the RBS of the putative essential gene or targeting the RBS of the lead gene of the polycistron gene cluster. The putative essential gene is a gene not found in humans. In some embodiments, the method of assaying includes inducing expression of the RNA Regulator (5). In some embodiments, the method of assaying includes inducing expression of the RNA Regulator (5) in the presence of an antibiotic. In some embodiments, the antibiotic is added to the organism culture either prior to or after the binding of the ribosomal binding site (RBS) of the transcript of the putative essential gene or lead gene of the polycistron gene cluster.

Figure 6:
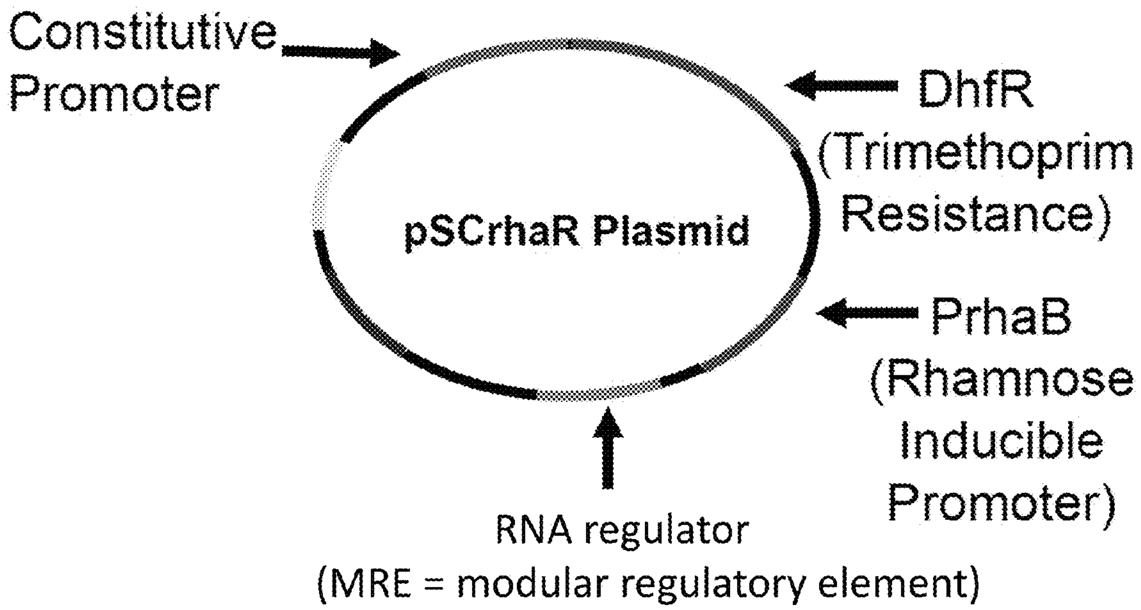
FIG. 6 is a schematic of the pSCPrhaB2 plasmid having a modular regulatory element (MRE) cassette (orange) for insertion and transcription of a selected RNA Regulator sequence under the control of the rhamnose inducible promoter (PrhaB)(green), according to embodiments of the present invention.
Figure 7A:
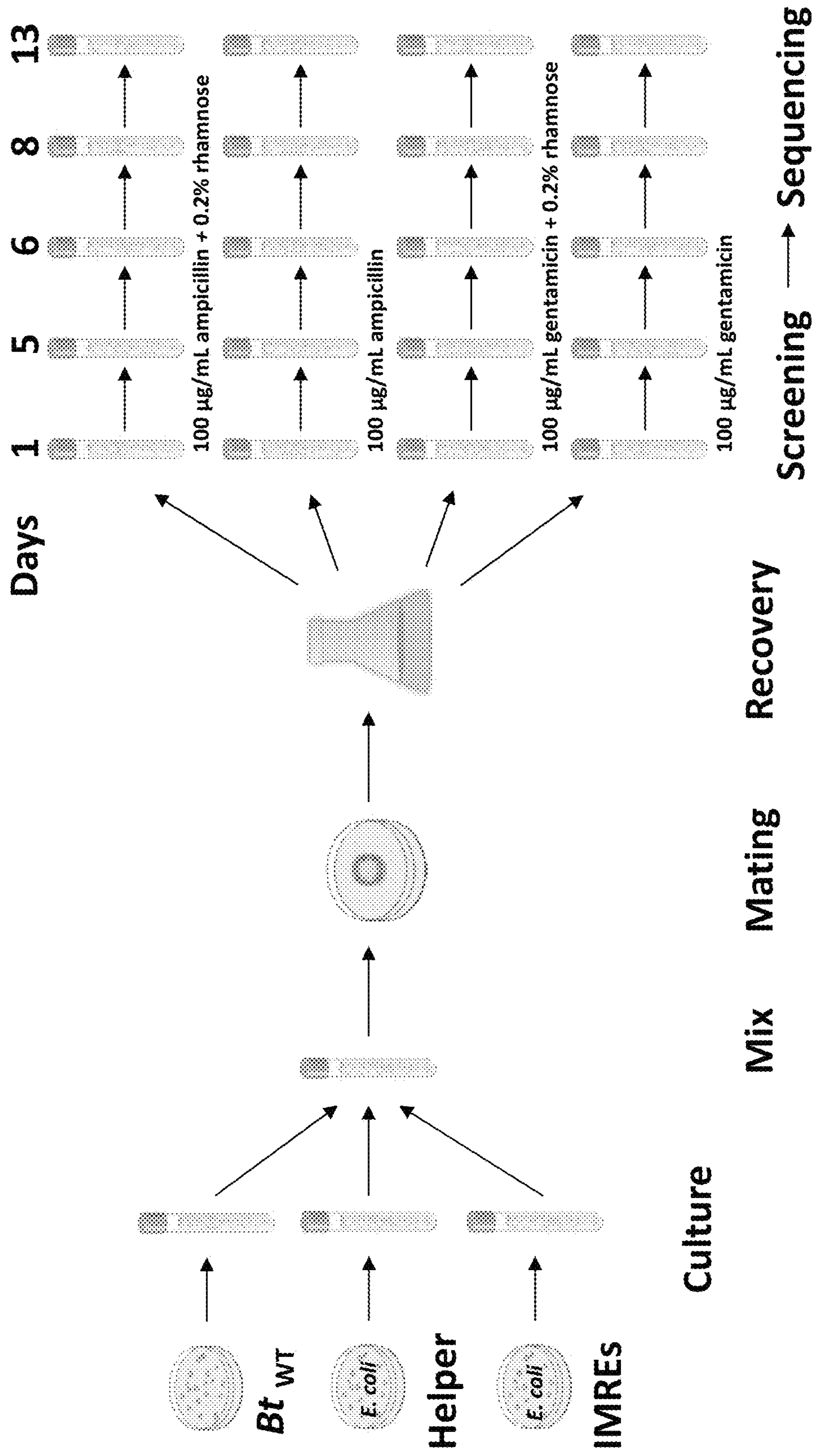
FIG. 7A is a schematic depicting method steps for a novel drug targeting screening of a library of MREs in *B. thailandensis*, including mating, growth, and sample collection process for screening and subsequent deep sequencing, according to embodiments of the present invention.
Figure 8B:
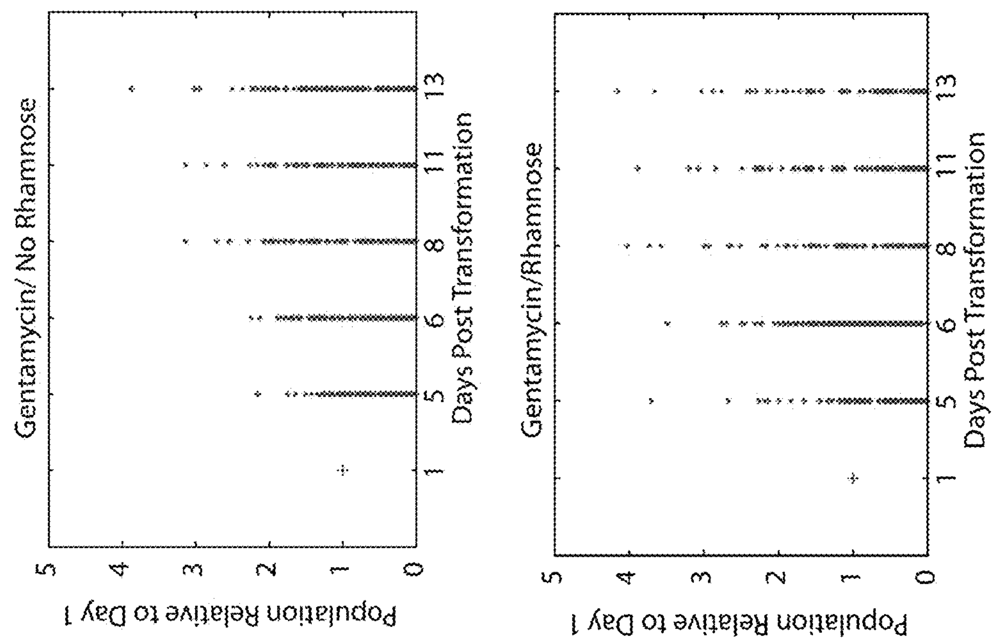
FIG. 8B shows data plots tracking the relative abundance growth in Bt for 500 different MREs as a function of time for a Bt MRE library in which the upper plot shows the relative abundance growth of Bt in the presence of gentamicin and no rhamnose, and the lower plot shows the relative abundance growth of Bt in the presence of gentamicin and rhamnose, according to embodiments of the present invention.
Figure 8A:
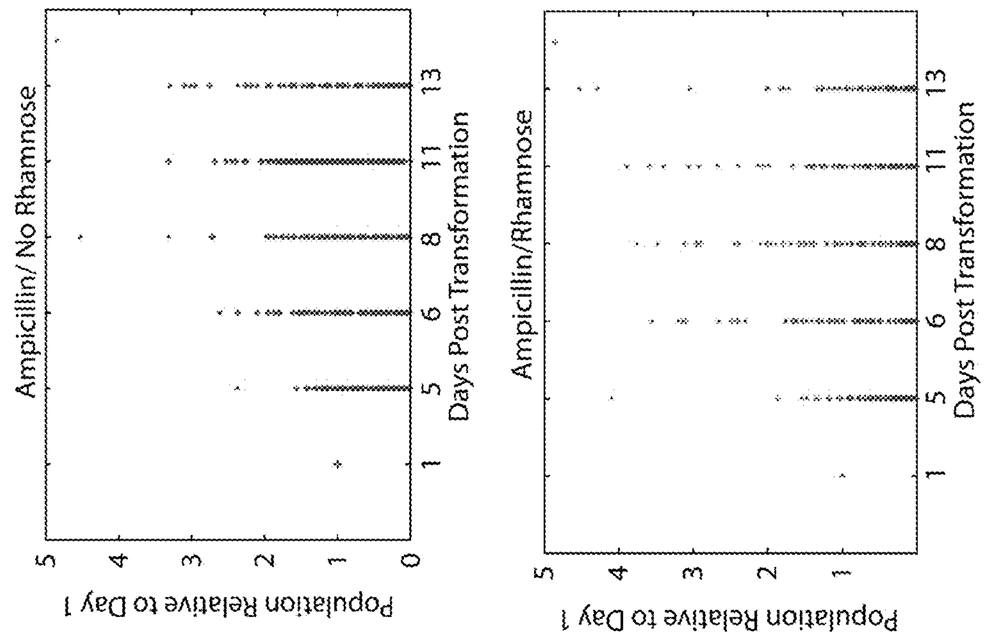
FIG. 8A shows data plots tracking the relative abundance growth in Bt for 500 different MREs as a function of time for a Bt MRE library in which the upper plot shows the relative abundance growth of Bt in the presence of ampicillin and no rhamnose and the lower plot shows the relative abundance growth of Bt in the presence of ampicillin and rhamnose, according to embodiments of the present invention.
Figure 8C:
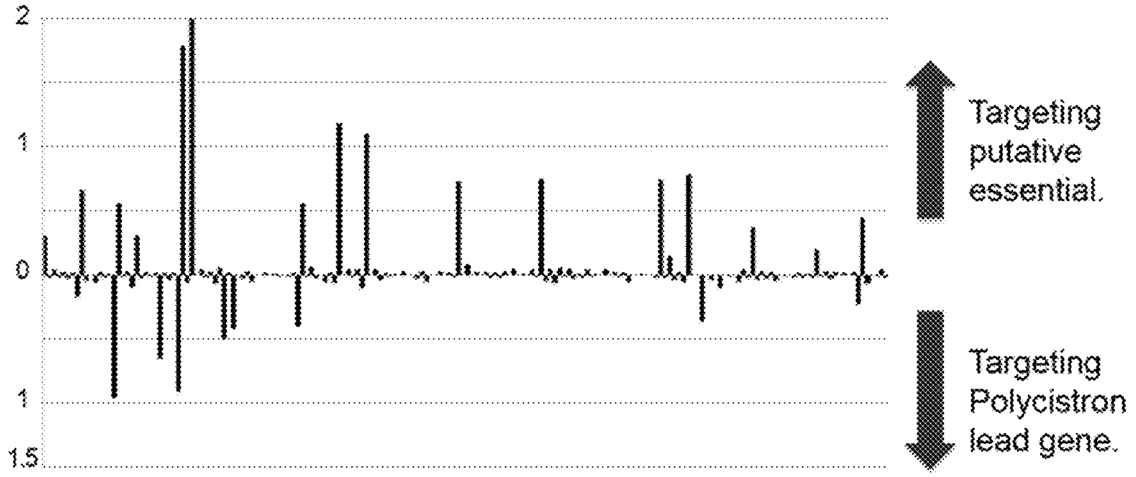
FIG. 8C is a graph plotting the data from FIGS. 8A and 8B as targets of putative essential genes or polycistronic lead genes, in which the bar plots represent the effects of the MREs of the individual putative essential genes (values less than 0) or when targeted as part of a polycistron (values greater than 0), according to embodiments of the present invention.

With reference to FIG. 6, each of the specifically constructed RNA Regulators (5) was separately cloned into a pSCPrhaB2 plasmid with transcription induced in the presence of rhamnose. The transformation and screening (i.e. selection) of this library of 500 RNA Regulators in Bt is shown in FIG. 7A with the relative abundance growth plots under the selective conditions shown in FIGS. 8A and 8B. The bar plot in FIG. 8C plots the data from FIGS. 8A and 8B showing that for some target genes, targeting the lead gene of a polycistron is required to knock-down or inhibit expression.

The following Examples are presented for illustrative purposes only, and do not limit the scope or content of the present application.

EXAMPLES

Example 1

Materials and Methods. Vector PMo168 is described in Hamad et al., Gene, 2009, 430:123-31, the entire content of which is incorporated herein by reference, and vector pSCPrhaB2 is described in Cardona et al., Plasmid, 2005, 54:219-28, the entire content of which is incorporated herein by reference.

Example 2

RNA Regulator (5) Sequences. For transcription of the RNA Regulators, DNA constructs were synthesized for plasmid expression. The complete DNA sequence for the AmrA RNA Regulator construct for insertion into vector pSCPrhaB2 or pMo168 is (SEQ ID NO: 4) GAATTCCATTCGAGCCTCTCCTTCTATCGGCGTGTGACGAGAAATCGTAATGCGTC GATAGAAGGAGAGGTTCGAATTATACATGTTATCAGCGCATGCGTGCCCAT CGTA TTTCATCGTTTTCCTCGCAAGTCGCTCGACCGGGACGAATTGCGATCGCGATATCA ATAAAACGAAAGGCTCAGTCGAAAGACTGGGCCTTTCGTTTTATCTGTTGCTGCAG CTCTAGA.

The SEQ ID NO: 4 AmrA DNA construct is made up of: an EcoRI restriction site GAATTC a spacer of one nucleotide (C), a 5'-Stem loop (10) (SEQ ID NO: 5), ATTCGAGCCTCTCCTTCTATCGGCGTGTGACGAGAAATCGTAATGCGTCGATAGAA GGAGAGGTTCGAAT a spacer of 3 nucleotides (TAT), an PciI restriction site ACATGT an AmrA targeting sequence (15) (SEQ ID NO: 6), TATCAGCGCATGCGTGCCCATTCGTATTTCATCGTTTTCCTCGCAAGTCGCTCGAC CGGGACGAATT an AsisI restriction site GCGATCGC a spacer of 3 nucleotides (GAT),a 3' Terminator (SEQ ID NO: 7), ATCAATAAAACGAAAGGCTCAGTCGAAAGACTGGGCCTTTCGTTTTATCTGTTG a spacer of 7 nucleotides (CTGCAGC) and a XbaI restriction site TCTAGA

Example 3

Design of a Modular Regulatory Element (MRE) Targeting Gentamicin Resistance ($AmrA_{MRE}$ or $AmrA_{MRE}$). AmrA is a periplasmic protein that links the transmembrane domains of the AmrAB-OprA pump that is responsible for gentamicin antibiotic resistance as well as resistance to other antibiotics. The initial cassette contains an MRE targeting sequence for AmrA ($Amr_{AMRE}$)(SEQ ID NO: 4) driven by the strong P1 promoter for constitutive transcription in *Burkholderia thailandensis*.

$AmrA_{MRE}$ P1 promoter cassette SEQ ID NO: 8: GATATCGAGACGAACCCAGTTGACATAAGCCTGTTCGGTTCGTAAACTGTAATGCA AGTAGCGTATGCGCTCACGCAACTGGTCCAGAACCTTGACCGAACGCAGCGGTGG TAACGGCGCAGTGGCGGTTTTCATGGCTTGTTATGACTGTTTTTTTGTACAGTCTAG CCTCGGGCATCCAAGCTAGCTAAGCGCGTTACGCCGTGGGTCGATGTTTGATGTT ATGGAACAGCAACGATGTTACGCAGCAGGGTAGTCGCCCTAAAACAAAGTTAGGC AGCCGTTGTGCTGGTGCTTTCTAGTAGTTGTTGTGGGGTAGGCAGTCAGAGTTCG ATTTGCTTGTCGCCATAATAGATTCACAAGAAGGATTCGACATGGGTCAAAGTACA TTCGAGCCTCTCCTTCTATCGGCGTGTGACGAGAAATCGTAATGCGTCGATAGAAG GAGAGGTTCGAATTATACATGTTATCAGCGCATGCGTGCCCATTCGTATTTCATCG TTTTCCTCGCAAGTCGCTCGACCGGGACGAATTGCGATCGCGATATCAATAAAACG AAAGGCTCAGTCGAAAGACTGGGCCTTTCGTTTTATCTGTTGCTGCAGCGATATC.

Example 4

Design of Modular Regulatory Elements targeting ciprofloxacin resistance ($RecA_{MRE}$/$RecA_{MRE}$ and $AmrA_{MRE}$/$AmrA_{MRE}$). The RecA and AmrA gene products have been identified as co-resistance mechanisms against ciprofloxacin treatment. RecA is responsible for activating the repair of the DNA that is cleaved by the action of ciprofloxacin and AmrA is part of the multidrug efflux pump. A vector was created allowing for, simultaneously, the constitutive expression of the AmrAMRE and an inducible expressed MRE targeting RecA ($RecA_{MRE}$). Here the targeting sequence for AmrA was swapped for one targeting RecA in the pSCPrhaB2-MRE. The constitutive P1-$AmrA_{MRE}$ cassette was then inserted at a second site in the vector creating pSCPrhaB2-$MRE_2$ as shown in FIG. 5A with a RecAMRE sequence of (SEQ ID NO: 17): GAATTC-C-ATTCGAGCCTCTCCTTCTATCGGCGTGTGACGAGAAATCGTAATGCGTCGATAGAA GGAGAGGTTCGAATTATACATGTTATCACAGCCCGGAGCCTTTCTTGCTTTC TTCC ATGAATCGTCCTTTGCTATGATGAGCAGCGTCTTGCGATCGCGATATCAATAAAAC GAAAGGCTCAGTCGAAAGACTGGGCCTTTCGTTTTATCTGTTGCTGCAGCTCTAGA

Example 5

Design of Modular Regulatory Elements targeting putative essential genes in *Burkholderia thailandensis* (Bt). A list of the putative essential genes from *Burkholderia* pseudiomallei (Bp) was obtained from Chong et al. 2006, supra. The list of genes from Bp was converted to a list of homologs in Bt using a custom software program, but could be obtained using the Basic Local Alignment Search Tool (BLAST). Targeting sequences that bind to the ribosomal binding site (RBS) of each putative gene were extracted automatically from the genomic sequence. These extracted targeting sequences are then synthesized and combined to create a library of RNA Regulators (MREs) specific for each of the putative essential genes. This MRE library was then inserted into the pSCPrhaB2 plasmid shown in FIG. 6 using Gibson assembly.

Example 6

Incorporation of MRE expression vectors into Bt. A modification of the triparental mating method developed for *Burkholderia gladioli* as described in Somprasong et al., 2010 was used to transform the expression vectors into Bt. (Somprasong et al., 2010, "Methods for genetic manipulation of *Burkholderia gladioli* pathovar *cocovenenans,*" *BMC Res Notes,* 3:308, the entire content of which is incorporated herein by reference.) Briefly, 8 mls of the following strains were grown overnight: Bt E264 (LB broth, carbenicillin 50 μg/ml; *E. coli* DH5-α cells containing the triparental Helper vector (LB, kanamycin 50 μg/ml); and *E. coli* DH5-α cells containing pSCPrhaB2-MRE (LB, trimethoprim 50 μg/ml. The outgrowth was approximately equivalent for all cultures and each culture of cells was pelleted and washed 3 times with LB broth and resuspended in a final volume of 200 µl. 80 µl of the donor and helper were then combined and 80 µls of the mix was transferred to the Bt tube and mixed. The samples were then placed at 30° C. for 1 hour and the contents were spread on LB plates without antibiotic and incubated overnight at 30° C. Plates were then scraped with 2 mls of LB. 25 µl from each scraped culture were plated (LB trimethoprim 50 µg/ml, gentamicin 50 µg/ml to assess the mating efficiency. These test plates showed no growth for the Donor/helper control. The remainder of the 2 ml mating sample was then transferred to 100 ml LB with trimethoprim 50 µg/ml and gentamicin 50 µg/ml and grown overnight at 30° C.

Example 7

Activity Screening of MREs. MREs targeting the gentamicin and ciprofloxacin antibiotic resistance mechanisms were screened for activity by monitoring their effect on Bt growth in the presence of the antibiotics.

Figure 4C:
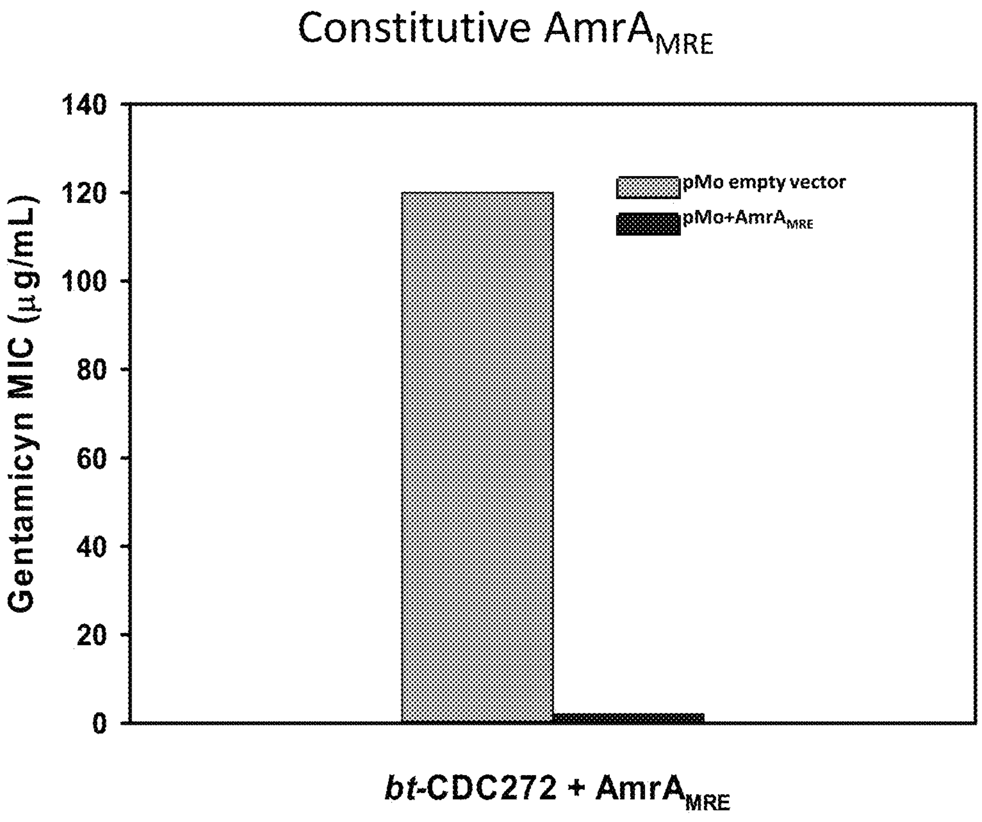
FIG. 4C is a graph of the growth of the pathogenic Bt-CDC272 in the presence of gentamicin at the indicated minimum inhibitory concentration (MIC) ug/mL, without an RNA Regulator (pMO empty vector, green) and with the pMO168-$Amr_{AMRE}$ plasmid (pMo+$Amr_{AMRE}$, low growth observed in maroon on right) constitutively expressing a target sequence that inhibits the AmrA gene translation, according to embodiments of the present invention.

Activity screening for $AmrA_{MRE}$. The screening of the activity of the constitutively expressed and inducible versions of the $AmrA_{MRE}$ against gentamicin resistance was performed by incubating $AmrA_{MRE}$ expressing *B. thailandensis* overnight in the presence of increasing concentrations of gentamicin, from 0 to 400 µg/mL as shown in FIG. 4B. In addition the constitutive $AmrA_{MRE}$ was also tested with the pathogenic version of *B. thailandensis* (Bt-CDC272) and the results as shown in FIG. 4C were comparable to those of the non-pathogenic Bt.

Figure 5B:
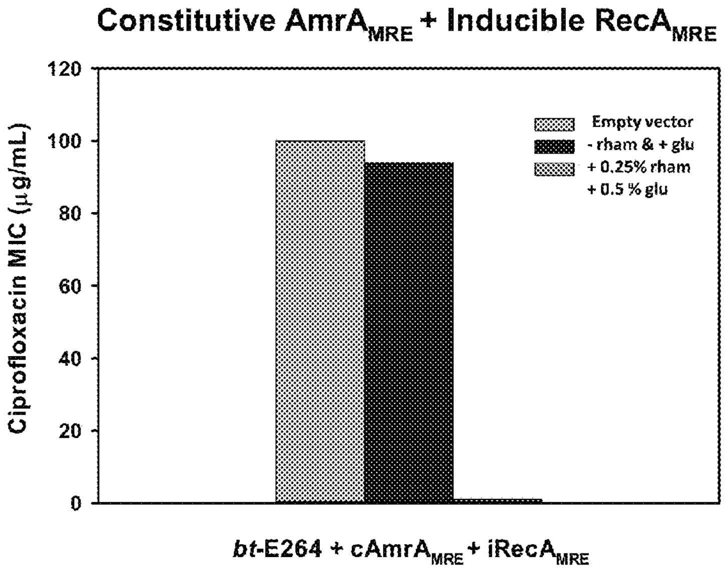
FIG. 5B is a graph of the growth of Bt-E264 in the presence of ciprofloxacin at the indicated minimum inhibitory concentration (MIC) μg/mL, without a plasmid (empty vector, green shown on left), with the pSCPrhaB2-$cAmr_{AMRE}$-$iRec_{AMRE}$ plasmid of FIG. 5A in the presence of glucose only (−rham+gluc, shown in maroon), and in the presence of glucose and rhamnose (+0.25% rham+0.5% glu, minimal growth shown in orange), according to embodiments of the present invention.

Activity screening for $RecA_{MRE}$/$AmrA_{MRE}$. The screening of the activity of the constitutively expressed $AmrA_{MRE}$ and inducible $RecA_{MRE}$ against ciprofloxacin resistance was performed by incubating $RecA_{MRE}$/$AmrA_{MRE}$ expressing *B. thailandensis* overnight in the presence of increasing concentrations of ciprofloxacin, from 0 to 100 µg/mL. The expression of the RecAMRE was induced by the addition of 0.2% rhamnose as shown in FIG. 5B.

Figure 7B:
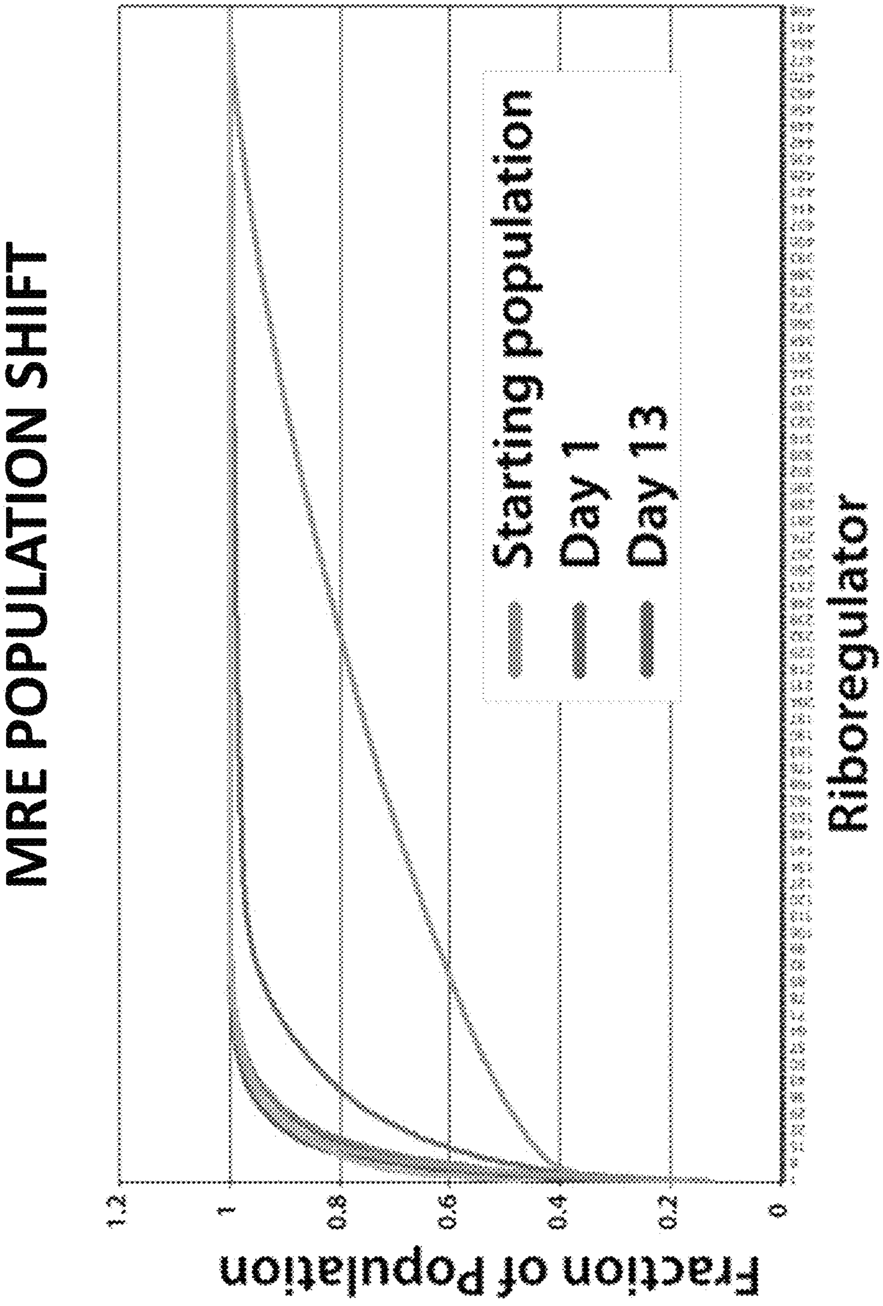
FIG. 7B is a graph plotting the fraction of the population relative to the number of MREs (Riboregulators) at day 0 (green), day 1 (blue), and day 13 (red) of the library screen of FIG. 7A, according to embodiments of the present invention.

Activity screening for the Bt MRE library targeting all putative essential genes. The screening of the activity of the inducible expressed Bt MRE library was performed by incubating the Bt MRE library expressing *B. thailandensis* for 13 days in the absence and presence of 0.2% rhamnose as shown in FIG. 7A. AmrA was used as the positive control for this experiments and the Bt MRE library (containing $AmrA_{MRE}$) expressing *B. thailandensis* was also incubated with and without gentamicin to confirm the activity of the MREs, specifically the activity of the $AmrA_{MRE}$ as shown in FIGS. 8A and 8B and then plotted as targeting a putative essential gene or polycistronic lead gene as shown in FIG. 8C. After transformation of the MRE library into Bt cells, the cells were grown overnight and four large 500 mL cultures were inoculated with the cells and supplemented with the rhamnose and gentamicin as described in the above conditions. Aliquots (8 mL) were collected at the specific intervals (Day 1, 5, 6, 8 and 13) and the vectors containing the MRE targeting genes in the library were purified by Mini-Prep and PCR barcoded by day and condition. The PCR products from each day and condition were collected, quantified and mixed, followed by deep sequencing using an Illumina miSeq platform. Data were analyzed using a custom software program to extract, identify, and quantify the targeting sequences from each time point and condition. FIG. 7A illustrates the mating (transformation, steps 1 to 5) and sample collection process and FIG. 7B shows an increase in the fraction of the population with MRE targeting genes over the 13 day time course While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A ribonucleic acid (RNA) composition for inhibiting translation of a bacterial target gene transcript, the RNA composition comprising:

a first segment of RNA capable of forming a 5' stem loop structure, the first segment of RNA comprising a sequence of SEQ ID NO: 1, 2, 9, 10, 11, or 12;

a second segment of RNA downstream of the first segment of RNA, the second segment comprising a targeting sequence capable of binding to a ribosomal binding site (RBS) of the bacterial target gene transcript; and a third segment of RNA downstream of the second segment of RNA, the third segment capable of forming a 3' terminator downstream of the targeting sequence, the third segment of RNA comprising a sequence of SEQ ID NO: 3.

2. The RNA composition of claim 1, wherein the targeting sequence is complementary to the RBS of the bacterial target gene transcript.

3. The RNA composition of claim 1, wherein the bacterial target gene transcript is part of a polycistron.

* * * * *

SEQUENCE LISTING

```
<160> NUMBER OF SEQ ID NOS: 17

<210> SEQ ID NO 1
<211> LENGTH: 70
<212> TYPE: RNA
<213> ORGANISM: Artificial Sequence
<220> FEATURE:
<223> OTHER INFORMATION: 5' Stem Loop 1

<400> SEQUENCE: 1

auucgagccu cuccuucuau cggcguguga cgagaaaucg uaaugcgucg auagaaggag      60

agguucgaau                                                             70


<210> SEQ ID NO 2
<211> LENGTH: 70
<212> TYPE: RNA
<213> ORGANISM: Artificial Sequence
<220> FEATURE:
<223> OTHER INFORMATION: 5' Stem Loop 2

<400> SEQUENCE: 2

uaagcuugga gaggaagaua gcugcguaau gcuaaagagc agugugcggc uaucuuccuc      60

uccgagcuua                                                             70


<210> SEQ ID NO 3
```

-continued

```
<211> LENGTH: 54
<212> TYPE: RNA
<213> ORGANISM: Artificial Sequence
<220> FEATURE:
<223> OTHER INFORMATION: 3' Terminator

<400> SEQUENCE: 3

aucaauaaaa cgaaaggcuc agucgaaaga cugggccuuu cguuuuaucu guug           54


<210> SEQ ID NO 4
<211> LENGTH: 231
<212> TYPE: DNA
<213> ORGANISM: Artificial Sequence
<220> FEATURE:
<223> OTHER INFORMATION: AmrA Regulator Vector Insert

<400> SEQUENCE: 4

gaattccatt cgagcctctc cttctatcgg cgtgtgacga gaaatcgtaa tgcgtcgata     60

gaaggagagg ttcgaattat acatgttatc agcgcatgcg tgcccattcg tatttcatcg    120

ttttcctcgc aagtcgctcg accgggacga attgcgatcg cgatatcaat aaaacgaaag    180

gctcagtcga aagactgggc ctttcgtttt atctgttgct gcagctctag a             231


<210> SEQ ID NO 5
<211> LENGTH: 70
<212> TYPE: DNA
<213> ORGANISM: Artificial Sequence
<220> FEATURE:
<223> OTHER INFORMATION: 5' Stem Loop 1 DNA

<400> SEQUENCE: 5

attcgagcct ctccttctat cggcgtgtga cgagaaatcg taatgcgtcg atagaaggag     60

aggttcgaat                                                            70


<210> SEQ ID NO 6
<211> LENGTH: 67
<212> TYPE: DNA
<213> ORGANISM: Artificial Sequence
<220> FEATURE:
<223> OTHER INFORMATION: AmrA targeting sequence

<400> SEQUENCE: 6

tatcagcgca tgcgtgccca ttcgtatttc atcgttttcc tcgcaagtcg ctcgaccggg     60

acgaatt                                                               67


<210> SEQ ID NO 7
<211> LENGTH: 54
<212> TYPE: DNA
<213> ORGANISM: Artificial Sequence
<220> FEATURE:
<223> OTHER INFORMATION: 3' Terminator DNA

<400> SEQUENCE: 7

atcaataaaa cgaaaggctc agtcgaaaga ctgggccttt cgttttatct gttg           54


<210> SEQ ID NO 8
<211> LENGTH: 612
<212> TYPE: DNA
<213> ORGANISM: Artificial Sequence
<220> FEATURE:
<223> OTHER INFORMATION: AmrA P1 promoter

<400> SEQUENCE: 8

gatatcgaga cgaacccagt tgacataagc ctgttcggtt cgtaaactgt aatgcaagta     60
```

-continued

```
gcgtatgcgc tcacgcaact ggtccagaac cttgaccgaa cgcagcggtg gtaacggcgc    120

agtggcggtt ttcatggctt gttatgactg tttttttgta cagtctagcc tcgggcatcc    180

aagctagcta agcgcgttac gccgtgggtc gatgtttgat gttatggaac agcaacgatg    240

ttacgcagca gggtagtcgc cctaaaacaa agttaggcag ccgttgtgct ggtgctttct    300

agtagttgtt gtggggtagg cagtcagagt tcgatttgct tgtcgccata atagattcac    360

aagaaggatt cgacatgggt caaagtacat tcgagcctct ccttctatcg gcgtgtgacg    420

agaaatcgta atgcgtcgat agaaggagag gttcgaatta tacatgttat cagcgcatgc    480

gtgcccattc gtatttcatc gttttcctcg caagtcgctc gaccgggacg aattgcgatc    540

gcgatatcaa taaaacgaaa ggctcagtcg aaagactggg cctttcgttt tatctgttgc    600

tgcagcgata tc                                                          612


<210> SEQ ID NO 9
<211> LENGTH: 52
<212> TYPE: RNA
<213> ORGANISM: Artificial Sequence
<220> FEATURE:
<223> OTHER INFORMATION: Stem Loop Helix 23-1

<400> SEQUENCE: 9

auucgagcca ucggcgugug acgagaaauc guaaugcguc gaugguucga au              52


<210> SEQ ID NO 10
<211> LENGTH: 52
<212> TYPE: RNA
<213> ORGANISM: Artificial Sequence
<220> FEATURE:
<223> OTHER INFORMATION: Stem Loop helix-23-2

<400> SEQUENCE: 10

uaagcucggu agccgcacac ugcucuuuag cauuacgcag cuaccaagcu ua              52


<210> SEQ ID NO 11
<211> LENGTH: 28
<212> TYPE: RNA
<213> ORGANISM: Artificial Sequence
<220> FEATURE:
<223> OTHER INFORMATION: Stem Loop helix-12-1

<400> SEQUENCE: 11

auucgagcca uagaaauaug guucgaau                                         28


<210> SEQ ID NO 12
<211> LENGTH: 28
<212> TYPE: RNA
<213> ORGANISM: Artificial Sequence
<220> FEATURE:
<223> OTHER INFORMATION: Stem loop helix-12-2

<400> SEQUENCE: 12

uaagcucggu aucuuuauac caagcuua                                         28


<210> SEQ ID NO 13
<211> LENGTH: 52
<212> TYPE: DNA
<213> ORGANISM: Artificial Sequence
<220> FEATURE:
<223> OTHER INFORMATION: Stem Loop helix-23-1 DNA

<400> SEQUENCE: 13
```

-continued

```
attcgagcca tcggcgtgtg acgagaaatc gtaatgcgtc gatggttcga at            52


<210> SEQ ID NO 14
<211> LENGTH: 52
<212> TYPE: DNA
<213> ORGANISM: Artificial Sequence
<220> FEATURE:
<223> OTHER INFORMATION: Stem Loop helix-23-2 DNA

<400> SEQUENCE: 14

taagctcggt agccgcacac tgctctttag cattacgcag ctaccaagct ta            52


<210> SEQ ID NO 15
<211> LENGTH: 28
<212> TYPE: DNA
<213> ORGANISM: Artificial Sequence
<220> FEATURE:
<223> OTHER INFORMATION: Stem Loop helix-12-1 DNA

<400> SEQUENCE: 15

attcgagcca tagaaatatg gttcgaat                                        28


<210> SEQ ID NO 16
<211> LENGTH: 28
<212> TYPE: DNA
<213> ORGANISM: Artificial Sequence
<220> FEATURE:
<223> OTHER INFORMATION: Stem Loop helix-12-2 DNA

<400> SEQUENCE: 16

taagctcggt atctttatac caagctta                                        28


<210> SEQ ID NO 17
<211> LENGTH: 231
<212> TYPE: DNA
<213> ORGANISM: Artificial Sequence
<220> FEATURE:
<223> OTHER INFORMATION: RecA MRE Vector Insert

<400> SEQUENCE: 17

gaattccatt cgagcctctc cttctatcgg cgtgtgacga gaaatcgtaa tgcgtcgata     60

gaaggagagg ttcgaattat acatgttatc acagcccgga gcctttcttg ctttcttcca    120

tgaatcgtcc tttgctatga tgagcagcgt cttgcgatcg cgatatcaat aaaacgaaag    180

gctcagtcga aagactgggc ctttcgtttt atctgttgct gcagctctag a             231
```